(12) United States Patent
Hudspeth et al.

(10) Patent No.: US 9,974,890 B2
(45) Date of Patent: *May 22, 2018

(54) WOUND THERAPY SYSTEM AND RELATED METHODS THEREFOR

(71) Applicant: Smith & Nephew, Inc., Memphis, TN (US)

(72) Inventors: Michael D. Hudspeth, Arnold, MO (US); Kenneth M. Breitweiser, Brighton, IL (US); Ricky A. Sisk, Washington, MO (US); Michael C. Dorsey, Edwardsville, IL (US)

(73) Assignee: Smith & Nephew, Inc., Memphis, TN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/192,605

(22) Filed: Jun. 24, 2016

(65) Prior Publication Data

US 2016/0325025 A1 Nov. 10, 2016

Related U.S. Application Data

(60) Division of application No. 14/486,338, filed on Sep. 15, 2014, now Pat. No. 9,375,521, which is a
(Continued)

(51) Int. Cl.
*A61M 1/00* (2006.01)
*A61M 27/00* (2006.01)
*A61M 39/24* (2006.01)

(52) U.S. Cl.
CPC ........ *A61M 1/0017* (2014.02); *A61M 1/0001* (2013.01); *A61M 1/005* (2014.02);
(Continued)

(58) Field of Classification Search
CPC .. A61M 1/0017; A61M 1/0033; A61M 1/005; A61M 1/0052; A61M 1/0001;
(Continued)

(56) References Cited

U.S. PATENT DOCUMENTS

| | | |
|---|---|---|
| 730,062 A | 6/1903 | Widmer |
| 2,468,445 A | 4/1949 | Hurst |

(Continued)

FOREIGN PATENT DOCUMENTS

| | | |
|---|---|---|
| CN | 2623320 | 7/2004 |
| DE | 39 16 648 | 9/1990 |

(Continued)

OTHER PUBLICATIONS

U.S. Appl. No. 14/019,932 (Iss'd U.S. Pat. No. 9,050,399) filed Sep. 6, 2013, Hartwell.
(Continued)

*Primary Examiner* — Philip R Wiest
(74) *Attorney, Agent, or Firm* — Knobbe, Martens, Olson & Bear, LLP

(57) ABSTRACT

A portable system for subatmospheric pressure therapy in connection with healing a surgical wound, including a wound dressing dimensioned for positioning relative to a wound bed of a subject and a subatmospheric pressure mechanism dimensioned to be carried or worn by the subject. The subatmospheric pressure mechanism includes a housing having a control unit adapted to draw a vacuum and a canister associated with the housing. The canister has a collection bag disposed therein, which is in fluid communication with the wound dressing to receive exudates from the wound bed. The collection bag is adapted to expand upon receipt of the fluids and has means to release gas from within the collection bag in connection with operation of the control unit. With this arrangement, the canister is attitude (Continued)

independent, i.e., the canister may be positioned on edge, on its side or on its end etc. while still maintaining operation of the control unit. The collection bag may include a hydrophobic vent or material for releasing the gases. In another embodiment, the collection bag comprises a gas permeable material. The collection bag may include one of pleats or bellows.

6 Claims, 8 Drawing Sheets

Related U.S. Application Data continuation of application No. 13/777,171, filed on Feb. 26, 2013, now Pat. No. 8,834,452, which is a continuation of application No. 12/124,707, filed on May 21, 2008, now Pat. No. 8,414,519.

(52) U.S. Cl.
CPC ........ *A61M 1/0011* (2013.01); *A61M 1/0023* (2013.01); *A61M 1/0033* (2014.02); *A61M 1/0052* (2014.02); *A61M 1/0088* (2013.01); *A61M 27/00* (2013.01); *A61M 39/24* (2013.01); *A61M 2205/21* (2013.01); *A61M 2205/7536* (2013.01); *A61M 2205/8206* (2013.01); *A61M 2205/8293* (2013.01); *A61M 2209/088* (2013.01)

(58) Field of Classification Search
CPC .............. A61M 1/0011; A61M 1/0023; A61M 1/0088; A61M 27/00; A61M 39/24; A61M 2205/21; A61M 2205/7536; A61M 2205/8206; A61M 2205/8293
See application file for complete search history.

(56) References Cited

U.S. PATENT DOCUMENTS

| | | |
|---|---|---|
| 3,704,709 A | 3/1972 | Sorenson et al. |
| 3,866,608 A | 2/1975 | Reynolds et al. |
| 3,980,166 A | 9/1976 | DeFeudis |
| 4,063,556 A | 12/1977 | Thomas et al. |
| 4,112,949 A | 9/1978 | Rosenthal et al. |
| 4,136,696 A | 1/1979 | Nehring |
| 4,203,445 A | 5/1980 | Jessup et al. |
| 4,228,798 A | 10/1980 | Deaton |
| 4,266,545 A | 5/1981 | Moss |
| 4,293,609 A | 10/1981 | Erickson |
| 4,296,748 A | 10/1981 | Kurtz et al. |
| 4,321,020 A | 3/1982 | Mital |
| 4,331,147 A | 5/1982 | Armstrong |
| 4,373,528 A | 2/1983 | Harle |
| 4,376,439 A | 3/1983 | Lauterjung |
| 4,402,687 A | 9/1983 | Denty et al. |
| 4,429,693 A | 2/1984 | Blake et al. |
| 4,460,642 A | 7/1984 | Errede et al. |
| 4,551,141 A | 11/1985 | McNeil |
| 4,569,674 A | 2/1986 | Phillips et al. |
| 4,573,992 A | 3/1986 | Marx |
| 4,578,060 A | 3/1986 | Huck et al. |
| 4,585,397 A | 4/1986 | Crawford et al. |
| 4,604,313 A | 8/1986 | McFarland et al. |
| 4,642,088 A | 2/1987 | Gunter |
| 4,642,093 A | 2/1987 | Harle |
| 4,655,754 A | 4/1987 | Richmond et al. |
| 4,675,010 A | 6/1987 | Siposs et al. |
| 4,706,830 A | 11/1987 | Wareing |
| 4,738,671 A | 4/1988 | Elliott et al. |
| 4,747,844 A | 5/1988 | Elliott |
| 4,758,238 A | 7/1988 | Sundblom et al. |
| 4,767,417 A | 8/1988 | Boehringer et al. |
| 4,769,019 A | 9/1988 | Kerwin |
| 4,798,578 A | 1/1989 | Ranford |
| 4,822,346 A | 4/1989 | Elliott |
| 4,826,494 A | 5/1989 | Richmond et al. |
| 4,828,546 A | 5/1989 | McNeil et al. |
| 4,832,299 A | 5/1989 | Gorton Lanny et al. |
| 4,850,964 A | 7/1989 | Cotter |
| 4,870,975 A | 10/1989 | Cronk et al. |
| 4,889,531 A | 12/1989 | D'Antonio et al. |
| 4,925,447 A | 5/1990 | Rosenblatt |
| 4,950,247 A | 8/1990 | Rosenblatt |
| 4,955,391 A | 9/1990 | Parker et al. |
| 4,976,694 A | 12/1990 | Schreibman |
| 4,979,944 A | 12/1990 | Luzsicza |
| 4,981,474 A | 1/1991 | Bopp et al. |
| 4,988,344 A | 1/1991 | Reising et al. |
| 4,988,345 A | 1/1991 | Reising |
| 4,990,137 A | 2/1991 | Graham |
| 5,002,529 A | 3/1991 | Cunningham |
| 5,002,534 A | 3/1991 | Rosenblatt |
| 5,053,026 A | 10/1991 | Andersen et al. |
| 5,055,198 A | 10/1991 | Shettigar |
| 5,073,172 A | 12/1991 | Fell |
| 5,112,323 A | 5/1992 | Winkler et al. |
| 5,135,485 A | 8/1992 | Cohen et al. |
| 5,141,504 A | 8/1992 | Herweck et al. |
| 5,149,325 A | 9/1992 | Telang et al. |
| 5,156,602 A | 10/1992 | Steffler |
| 5,158,533 A | 10/1992 | Strauss et al. |
| 5,188,622 A | 2/1993 | Muller et al. |
| 5,192,439 A | 3/1993 | Roth et al. |
| 5,219,428 A | 6/1993 | Stern |
| 5,246,353 A | 9/1993 | Sohn |
| 5,254,080 A | 10/1993 | Lindsay |
| 5,275,585 A | 1/1994 | Olson |
| 5,342,329 A | 8/1994 | Croquevielle |
| D352,463 S | 11/1994 | Kubo |
| 5,360,445 A | 11/1994 | Goldowsky |
| 5,374,257 A | 12/1994 | Drainville et al. |
| 5,382,244 A | 1/1995 | Telang |
| 5,386,735 A * | 2/1995 | Langdon ............ A61M 1/0001 73/863.23 |
| 5,397,299 A | 3/1995 | Karwoski et al. |
| 5,399,156 A | 3/1995 | Lindsay |
| 5,411,474 A | 5/1995 | Ott et al. |
| 5,466,229 A | 11/1995 | Elson |
| 5,470,585 A | 11/1995 | Gilchrist |
| 5,484,428 A | 1/1996 | Drainville et al. |
| 5,496,299 A | 3/1996 | Felix et al. |
| 5,542,939 A | 8/1996 | Onodera et al. |
| 5,545,151 A | 8/1996 | O'Connor et al. |
| 5,549,584 A | 8/1996 | Gross |
| 5,582,601 A | 12/1996 | Wortrich et al. |
| 5,584,824 A | 12/1996 | Gillette et al. |
| 5,588,958 A | 12/1996 | Cunningham et al. |
| 5,591,297 A | 1/1997 | Ahr |
| 5,630,855 A | 5/1997 | Lundbaeck |
| 5,636,643 A | 6/1997 | Argenta et al. |
| 5,645,081 A | 7/1997 | Argenta et al. |
| 5,656,027 A | 8/1997 | Ellingboe |
| 5,669,892 A | 9/1997 | Keogh et al. |
| 5,685,214 A | 11/1997 | Neff et al. |
| 5,688,516 A | 11/1997 | Raad et al. |
| 5,693,013 A | 12/1997 | Geuder |
| 5,707,173 A | 1/1998 | Cottone et al. |
| 5,762,638 A | 6/1998 | Shikani et al. |
| 5,776,118 A | 7/1998 | Seifert et al. |
| 5,785,700 A | 7/1998 | Olson |
| 5,787,928 A | 8/1998 | Allen et al. |
| 5,807,359 A | 9/1998 | Bemis et al. |
| D400,249 S | 10/1998 | Holubar et al. |
| 5,876,387 A | 3/1999 | Killian et al. |
| 5,882,743 A | 3/1999 | McConnell |
| D408,625 S | 4/1999 | Barker |
| 5,944,703 A | 8/1999 | Dixon et al. |
| 5,960,837 A | 10/1999 | Cude |
| 5,997,733 A | 12/1999 | Wilbur et al. |
| 6,010,527 A | 1/2000 | Augustine et al. |
| 6,071,267 A | 6/2000 | Zamierowski |

(56) References Cited

U.S. PATENT DOCUMENTS

| | | | |
|---|---|---|---|
| 6,075,177 A | 6/2000 | Bahia et al. |
| 6,093,230 A | 7/2000 | Johnson, III et al. |
| 6,099,493 A | 8/2000 | Swisher |
| 6,102,205 A | 8/2000 | Greff et al. |
| 6,142,982 A | 11/2000 | Hunt et al. |
| 6,152,902 A | 11/2000 | Christian et al. |
| 6,180,000 B1 | 1/2001 | Wilbur et al. |
| 6,261,276 B1 | 7/2001 | Reitsma |
| D449,891 S | 10/2001 | Norio Moro |
| 6,322,546 B1 | 11/2001 | Steg |
| 6,352,233 B1 | 3/2002 | Barberich |
| D456,514 S | 4/2002 | Brown et al. |
| 6,395,955 B1 | 5/2002 | Roe et al. |
| 6,458,109 B1 | 10/2002 | Henley et al. |
| 6,468,199 B1 | 10/2002 | Satou et al. |
| 6,478,774 B1 | 11/2002 | Balugani et al. |
| 6,501,002 B1 | 12/2002 | Roe et al. |
| D469,175 S | 1/2003 | Hall et al. |
| 6,547,255 B1 | 4/2003 | Donaway et al. |
| D475,132 S | 5/2003 | Randolph |
| 6,575,333 B1 | 6/2003 | Raboin |
| D477,869 S | 7/2003 | Vijfvinkel |
| D478,659 S | 8/2003 | Hall et al. |
| 6,620,379 B1 | 9/2003 | Pluk et al. |
| D481,459 S | 10/2003 | Werner Naham |
| 6,635,028 B1 | 10/2003 | Ielpo et al. |
| 6,648,862 B2 | 11/2003 | Watson |
| 6,685,681 B2 | 2/2004 | Lockwood et al. |
| 6,723,430 B2 | 4/2004 | Kurata et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,800,074 B2 | 10/2004 | Henley et al. |
| 6,820,483 B1 | 11/2004 | Beckerman |
| 6,824,533 B2 | 11/2004 | Risk, Jr. et al. |
| 6,856,075 B2 | 2/2005 | Johnson |
| 6,868,739 B1 | 3/2005 | Krivitski et al. |
| 6,885,116 B2 | 4/2005 | Knirck et al. |
| D504,953 S | 5/2005 | Bradley Peter Ryan |
| 6,936,037 B2 | 8/2005 | Bubb et al. |
| 6,951,553 B2 | 10/2005 | Bubb et al. |
| 6,955,664 B2 | 10/2005 | D'Antonio |
| 6,979,324 B2 | 12/2005 | Bybordi et al. |
| D516,217 S | 2/2006 | Brown et al. |
| 7,004,915 B2 | 2/2006 | Boynton et al. |
| D522,657 S | 6/2006 | Murphy et al. |
| 7,066,949 B2 | 6/2006 | Gammons et al. |
| 7,108,683 B2 | 9/2006 | Zamierowski |
| 7,128,735 B2 | 10/2006 | Weston |
| 7,153,294 B1 | 12/2006 | Farrow |
| D537,944 S | 3/2007 | Eda et al. |
| 7,198,046 B1 | 4/2007 | Argenta et al. |
| D544,092 S | 6/2007 | Lewis |
| 7,240,676 B2 | 7/2007 | Rutter |
| D548,347 S | 8/2007 | Ichino et al. |
| D551,578 S | 9/2007 | Kuriger et al. |
| D565,177 S | 3/2008 | Locke et al. |
| 7,381,859 B2 | 6/2008 | Hunt et al. |
| 7,438,705 B2 | 10/2008 | Karpowicz et al. |
| D580,285 S | 11/2008 | Hendrickson et al. |
| D581,042 S | 11/2008 | Randolph et al. |
| D581,522 S | 11/2008 | Randolph et al. |
| D585,137 S | 1/2009 | Onoda et al. |
| 7,503,910 B2 | 3/2009 | Adahan |
| D590,934 S | 4/2009 | Randolph et al. |
| D593,676 S | 6/2009 | Locke et al. |
| D594,114 S | 6/2009 | Locke et al. |
| 7,553,306 B2 | 6/2009 | Hunt et al. |
| 7,569,742 B2 | 8/2009 | Haggstrom et al. |
| D602,582 S | 10/2009 | Pidgeon et al. |
| D602,583 S | 10/2009 | Pidgeon et al. |
| D602,584 S | 10/2009 | Pidgeon et al. |
| 7,611,500 B1 | 11/2009 | Lina et al. |
| 7,615,036 B2 | 11/2009 | Joshi et al. |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| D617,094 S | 6/2010 | Pidgeon et al. |
| D617,461 S | 6/2010 | Kaushal et al. |
| 7,731,702 B2 | 6/2010 | Bybordi et al. |
| 7,758,554 B2 | 7/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| D625,801 S | 10/2010 | Pidgeon et al. |
| 7,846,141 B2 | 12/2010 | Weston |
| D630,313 S | 1/2011 | Pidgeon et al. |
| D630,725 S | 1/2011 | Pidgeon et al. |
| 7,862,339 B2 | 1/2011 | Mulligan |
| 7,927,318 B2 | 4/2011 | Risk, Jr. et al. |
| 7,964,766 B2 | 6/2011 | Blott et al. |
| 7,998,125 B2 | 8/2011 | Weston |
| 8,021,348 B2 | 9/2011 | Risk, Jr. et al. |
| 8,048,046 B2 | 11/2011 | Hudspeth et al. |
| 8,061,360 B2 | 11/2011 | Locke et al. |
| 8,062,272 B2 | 11/2011 | Weston |
| 8,080,702 B2 | 12/2011 | Blott et al. |
| 8,100,873 B2 | 1/2012 | Jaeb et al. |
| 8,172,817 B2 | 5/2012 | Michaels et al. |
| 8,240,470 B2 | 8/2012 | Pidgeon et al. |
| 8,246,607 B2 | 8/2012 | Karpowicz et al. |
| 8,257,327 B2 | 9/2012 | Blott et al. |
| 8,267,909 B2 | 9/2012 | Clementi et al. |
| 8,267,918 B2 | 9/2012 | Johnson et al. |
| 8,294,586 B2 | 10/2012 | Pidgeon et al. |
| 8,308,714 B2 | 11/2012 | Weston et al. |
| 8,323,264 B2 | 12/2012 | Weston et al. |
| 8,333,744 B2 | 12/2012 | Hartwell et al. |
| 8,372,049 B2 | 2/2013 | Jaeb et al. |
| 8,372,050 B2 | 2/2013 | Jaeb et al. |
| 8,414,519 B2 * | 4/2013 | Hudspeth ............ A61M 1/0001 604/10 |
| 8,444,392 B2 | 5/2013 | Turner et al. |
| 8,460,255 B2 | 6/2013 | Joshi et al. |
| 8,494,349 B2 | 7/2013 | Gordon |
| 8,535,283 B2 | 9/2013 | Heaton et al. |
| 8,551,061 B2 | 10/2013 | Hartwell et al. |
| 8,556,871 B2 | 10/2013 | Mormino et al. |
| 8,569,566 B2 | 10/2013 | Blott et al. |
| 8,617,129 B2 | 12/2013 | Hartwell |
| 8,622,981 B2 | 1/2014 | Hartwell et al. |
| 8,641,691 B2 | 2/2014 | Fink et al. |
| 8,679,079 B2 | 3/2014 | Heaton et al. |
| 8,747,376 B2 | 6/2014 | Locke et al. |
| 8,771,259 B2 | 7/2014 | Karpowicz et al. |
| 8,814,840 B2 | 8/2014 | Evans et al. |
| 8,814,841 B2 | 8/2014 | Hartwell |
| 8,821,458 B2 | 9/2014 | Locke et al. |
| 8,834,452 B2 * | 9/2014 | Hudspeth ............ A61M 1/0001 604/313 |
| 8,843,327 B2 | 9/2014 | Vernon-Harcourt et al. |
| 8,845,603 B2 | 9/2014 | Middleton et al. |
| 8,864,748 B2 | 10/2014 | Coulthard et al. |
| 8,974,429 B2 | 3/2015 | Gordon et al. |
| 9,019,681 B2 | 4/2015 | Locke et al. |
| 9,050,399 B2 | 6/2015 | Hartwell |
| 9,205,183 B2 | 12/2015 | Hartwell et al. |
| 9,227,000 B2 | 1/2016 | Fink et al. |
| 9,320,838 B2 | 4/2016 | Hartwell et al. |
| 9,408,954 B2 | 8/2016 | Gordon et al. |
| 9,561,312 B2 | 2/2017 | Heaton et al. |
| 9,636,440 B2 | 5/2017 | Weston et al. |
| 9,642,955 B2 | 5/2017 | Fink et al. |
| 2002/0026160 A1 | 2/2002 | Takahashi et al. |
| 2002/0145012 A1 | 10/2002 | Ho |
| 2002/0156464 A1 | 10/2002 | Blischak et al. |
| 2003/0065292 A1 | 4/2003 | Darouiche |
| 2003/0093041 A1 | 5/2003 | Risk, Jr. et al. |
| 2003/0097100 A1 | 5/2003 | Watson |
| 2003/0101826 A1 | 6/2003 | Neubert |

(56) References Cited

U.S. PATENT DOCUMENTS

| | | |
|---|---|---|
| 2003/0164600 A1 | 9/2003 | Dunn et al. |
| 2003/0181850 A1 | 9/2003 | Diamond et al. |
| 2003/0235635 A1 | 12/2003 | Fong et al. |
| 2004/0006321 A1 | 1/2004 | Cheng et al. |
| 2004/0054338 A1* | 3/2004 | Bybordi ............... A61M 27/00 604/313 |
| 2004/0064132 A1 | 4/2004 | Boehringer et al. |
| 2004/0087918 A1 | 5/2004 | Johnson et al. |
| 2004/0102743 A1 | 5/2004 | Walker |
| 2004/0116551 A1 | 6/2004 | Terry |
| 2004/0122383 A1 | 6/2004 | Romano et al. |
| 2004/0167482 A1 | 8/2004 | Watson |
| 2004/0180093 A1 | 9/2004 | Burton et al. |
| 2004/0233631 A1 | 11/2004 | Lord |
| 2004/0260230 A1 | 12/2004 | Randolph |
| 2005/0070858 A1 | 3/2005 | Lockwood et al. |
| 2005/0124966 A1 | 6/2005 | Karpowicz et al. |
| 2005/0144711 A1 | 7/2005 | Valadez et al. |
| 2005/0166683 A1 | 8/2005 | Krivitski et al. |
| 2005/0187528 A1 | 8/2005 | Berg |
| 2005/0209560 A1 | 9/2005 | Boukhny et al. |
| 2005/0248045 A1 | 11/2005 | Anthony |
| 2006/0009744 A1 | 1/2006 | Erdman et al. |
| 2006/0029675 A1 | 2/2006 | Ginther |
| 2006/0059980 A1 | 3/2006 | Matsubara et al. |
| 2006/0129137 A1 | 6/2006 | Lockwood et al. |
| 2006/0144440 A1 | 7/2006 | Merkle |
| 2006/0149171 A1 | 7/2006 | Vogel et al. |
| 2007/0016152 A1 | 1/2007 | Karpowicz et al. |
| 2007/0027433 A1 | 2/2007 | Garcia et al. |
| 2007/0032741 A1 | 2/2007 | Hibner et al. |
| 2007/0032763 A1 | 2/2007 | Vogel |
| 2007/0055209 A1 | 3/2007 | Patel et al. |
| 2007/0078444 A1 | 4/2007 | Larsson |
| 2007/0118096 A1 | 5/2007 | Smith et al. |
| 2007/0135779 A1 | 6/2007 | Lalomia et al. |
| 2007/0141128 A1 | 6/2007 | Blott et al. |
| 2007/0179460 A1 | 8/2007 | Adahan |
| 2007/0180904 A1 | 8/2007 | Gao |
| 2007/0219513 A1 | 9/2007 | Lina et al. |
| 2007/0219532 A1 | 9/2007 | Karpowicz et al. |
| 2007/0219535 A1 | 9/2007 | Phung et al. |
| 2007/0233022 A1 | 10/2007 | Henley et al. |
| 2007/0244451 A1 | 10/2007 | Romano et al. |
| 2007/0260226 A1 | 11/2007 | Jaeb et al. |
| 2008/0011667 A1 | 1/2008 | Ruschke |
| 2008/0015526 A1 | 1/2008 | Reiner et al. |
| 2008/0033400 A1 | 2/2008 | Holper et al. |
| 2008/0051708 A1 | 2/2008 | Kumar et al. |
| 2008/0071234 A1 | 3/2008 | Kelch et al. |
| 2008/0071235 A1 | 3/2008 | Locke et al. |
| 2008/0082040 A1 | 4/2008 | Kubler et al. |
| 2008/0082077 A1 | 4/2008 | Williams |
| 2008/0108977 A1 | 5/2008 | Heaton et al. |
| 2008/0125697 A1 | 5/2008 | Gao |
| 2008/0125698 A1 | 5/2008 | Gerg et al. |
| 2008/0132855 A1 | 6/2008 | Romano et al. |
| 2008/0200905 A1 | 8/2008 | Heaton et al. |
| 2008/0234641 A1 | 9/2008 | Locke et al. |
| 2008/0243096 A1 | 10/2008 | Svedman |
| 2008/0281281 A1 | 11/2008 | Meyer et al. |
| 2009/0005746 A1 | 1/2009 | Nielsen et al. |
| 2009/0043268 A1 | 2/2009 | Eddy et al. |
| 2009/0101219 A1 | 4/2009 | Martini et al. |
| 2009/0157016 A1 | 6/2009 | Adahan |
| 2009/0204049 A1 | 8/2009 | Lee |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254066 A1 | 10/2009 | Heaton |
| 2009/0275922 A1 | 11/2009 | Coulthard et al. |
| 2009/0312725 A1 | 12/2009 | Braga |
| 2010/0022990 A1 | 1/2010 | Karpowicz et al. |
| 2010/0030132 A1 | 2/2010 | Niezgoda et al. |
| 2010/0036333 A1 | 2/2010 | Schenk, III et al. |
| 2010/0042059 A1 | 2/2010 | Pratt et al. |
| 2010/0121257 A1 | 5/2010 | King |
| 2010/0126268 A1 | 5/2010 | Baily et al. |
| 2010/0145289 A1 | 6/2010 | Line et al. |
| 2010/0211030 A1 | 8/2010 | Turner et al. |
| 2010/0268179 A1 | 10/2010 | Kelch et al. |
| 2010/0280435 A1 | 11/2010 | Raney et al. |
| 2010/0280536 A1 | 11/2010 | Hartwell |
| 2010/0305490 A1 | 12/2010 | Coulthard et al. |
| 2010/0324510 A1 | 12/2010 | Andresen et al. |
| 2011/0028918 A1 | 2/2011 | Hartwell |
| 2011/0054421 A1 | 3/2011 | Hartwell |
| 2011/0054810 A1 | 3/2011 | Turner |
| 2011/0063117 A1 | 3/2011 | Turner |
| 2011/0066110 A1 | 3/2011 | Fathallah et al. |
| 2011/0077605 A1 | 3/2011 | Karpowicz et al. |
| 2011/0092958 A1 | 4/2011 | Jacobs |
| 2011/0112493 A1 | 5/2011 | Koch et al. |
| 2011/0130712 A1 | 6/2011 | Topaz |
| 2011/0172615 A2 | 7/2011 | Greener |
| 2011/0172616 A1 | 7/2011 | Hartwell et al. |
| 2011/0251569 A1 | 10/2011 | Turner et al. |
| 2011/0295220 A1 | 12/2011 | Heaton et al. |
| 2012/0001762 A1 | 1/2012 | Turner et al. |
| 2012/0035560 A1 | 2/2012 | Eddy et al. |
| 2012/0041399 A1 | 2/2012 | Blott et al. |
| 2013/0090613 A1 | 4/2013 | Kelch et al. |
| 2013/0090615 A1 | 4/2013 | Jaeb et al. |
| 2013/0102979 A1 | 4/2013 | Coulthard et al. |
| 2013/0116635 A1 | 5/2013 | Fleischmann |
| 2013/0138054 A1 | 5/2013 | Fleischmann |
| 2013/0144235 A1 | 6/2013 | Augustine et al. |
| 2013/0338614 A1 | 12/2013 | Heaton et al. |
| 2014/0100538 A1 | 4/2014 | Hartwell |
| 2014/0100539 A1 | 4/2014 | Coulthard et al. |
| 2014/0155849 A1 | 6/2014 | Heaton et al. |
| 2014/0163491 A1 | 6/2014 | Schuessler |
| 2014/0188061 A1 | 7/2014 | Locke et al. |
| 2014/0200535 A1 | 7/2014 | Locke et al. |
| 2014/0236106 A1 | 8/2014 | Locke et al. |
| 2014/0276490 A1 | 9/2014 | Locke et al. |
| 2014/0276491 A1 | 9/2014 | Luckemeyer et al. |
| 2014/0276497 A1 | 9/2014 | Robinson |
| 2014/0309601 A1 | 10/2014 | Hall et al. |
| 2014/0320283 A1 | 10/2014 | Lawhorn |
| 2015/0073363 A1 | 3/2015 | Kelch et al. |
| 2015/0343122 A1 | 12/2015 | Hartwell |
| 2016/0144081 A1 | 5/2016 | Wiesner |
| 2016/0151547 A1 | 6/2016 | Hartwell et al. |
| 2016/0331877 A1 | 11/2016 | Braga et al. |

FOREIGN PATENT DOCUMENTS

| | | |
|---|---|---|
| DE | 43 12 852 | 10/1993 |
| EP | 0 358 302 | 3/1990 |
| EP | 1 476 217 B1 | 3/2008 |
| EP | 2 079 507 | 7/2009 |
| EP | 2 711 034 | 3/2014 |
| EP | 2 305 325 | 4/2014 |
| EP | 2 345 437 | 4/2014 |
| EP | 2 687 245 | 9/2014 |
| GB | 1 415 096 | 11/1975 |
| GB | 2235877 | 3/1991 |
| WO | WO 1987/00439 | 1/1987 |
| WO | WO 1996/05873 | 2/1996 |
| WO | WO 1996/19335 | 6/1996 |
| WO | WO 2003/074106 | 9/2003 |
| WO | WO 2003/101508 | 12/2003 |
| WO | WO 2004/060225 | 7/2004 |
| WO | WO 2005/105179 | 11/2005 |
| WO | WO 2005/123170 | 12/2005 |
| WO | WO 2006/052839 | 5/2006 |
| WO | WO 2008/036344 | 3/2008 |
| WO | WO 2008/036360 | 3/2008 |
| WO | WO 2008/039314 | 4/2008 |
| WO | WO 2008/048481 | 4/2008 |
| WO | WO 2009/004289 | 1/2009 |

(56) References Cited

FOREIGN PATENT DOCUMENTS

| WO | WO 2009/077722 | 6/2009 |
|----|----------------|--------|
| WO | WO 2009/086580 | 7/2009 |
| WO | WO 2009/124100 | 10/2009 |
| WO | WO 2009/151645 | 12/2009 |
| WO | WO 2010/017484 | 2/2010 |
| WO | WO 2010/039481 | 4/2010 |
| WO | WO 2014/113504 | 6/2014 |
| WO | WO 2014/107285 | 9/2014 |
| WO | WO 2014/143488 | 9/2014 |

OTHER PUBLICATIONS

U.S. Appl. No. 14/486,338 (Pub'd 2015/0073359) filed Sep. 15, 2014, Hudspeth et al.
U.S. Appl. No. 14/878,975, filed Oct. 8, 2015, Wudyka.
U.S. Appl. No. 15/493,058, filed Apr. 20, 2017, Fink et al.
U.S. Appl. No. 29/574,909, filed Aug. 19, 2016, Bjelovuk et al.
U.S. Appl. No. 29/574,925, filed Aug. 19, 2016, Bjelovuk et al.
The American Heritage® Science Dictionary Copyright © 2005, in 3 pages.
Huntleigh Healthcare, "Negative Pressure Positive Outcomes" WoundASSIST TNP Console and Canister Brochure, 2007, in 6 pages.
"Vivano—Product application description," Hartmann Vivano, http://www.vivanosystem.info/20809.php, accessed Feb. 28, 2013.

\* cited by examiner

ND RELATED METHODS THEREFOR

WOUND THERAPY SYSTEM AND RELATED METHODS THEREFOR

CROSS-REFERENCE TO RELATED APPLICATION

This application is a divisional application of co-pending U.S. application Ser. No. 14/486,338, filed on Sep. 15, 2014 and issued as U.S. Pat. No. 9,375,521, which is a continuation of U.S. application Ser. No. 13/777,171, filed on Feb. 26, 2013 and issued as U.S. Pat. No. 8,834,452, which is a continuation of and claims priority to U.S. application Ser. No. 12/124,707, filed May 21, 2008 and issued as U.S. Pat. No. 8,414,519.

BACKGROUND

Technical Field

The present disclosure relates to treating an open wound, and, more specifically, relates to a sub-atmospheric wound therapy system including a portable container adapted to maintain the operation of the system regardless of the orientation or positioning of the container.

Background of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure therapy also known as suction or vacuum therapy has been used in treating and healing wounds. Application of negative pressure, e.g. reduced or subatmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure therapy provides for a wound to be covered to facilitate suction at the wound area. A conduit is introduced through the wound covering to provide fluid communication to an external vacuum source. Atmospheric gas, wound exudates, or other fluids may thus be drawn from the reservoir through the fluid conduit to stimulate healing of the wound. Exudates drawn from the reservoir may be deposited in a collection canister or container.

The systems generally require that the container is maintained in a standing or upright position such that the fluid receiving reservoir within the respective unit may be vented and continue to receive fluid from the patient until the reservoir is full. Accidental tipping or tilting of the bag and/or container may cause the suction to/from the unit to be to be shut-off prior to the fluid receiving reservoir completely filling. This problem is further exaggerated in portable units which may be worn or carried by the subject.

SUMMARY

A portable system for subatmospheric pressure therapy in connection with healing a surgical wound includes a wound dressing dimensioned for positioning relative to a wound bed of a subject and a subatmospheric pressure mechanism dimensioned to be carried or worn by the subject. The subatmospheric pressure mechanism includes a housing having a control unit adapted to draw a vacuum and a canister associated with the housing. The canister has a collection bag disposed therein, which is in fluid communication with the wound dressing to receive exudates from the wound bed. The collection bag is adapted to expand upon receipt of the fluids and has means to release gas from within the collection bag in connection with operation of the control unit. With this arrangement, the canister is attitude independent, i.e., the canister may be positioned on edge, on its side or on its end etc. while still maintaining operation of the control unit. The collection bag may include a hydrophobic vent or material for releasing the gases. In another embodiment, the collection bag comprises a gas permeable material. The collection bag may include one of pleats or bellows.

In another embodiment, the portable system for subatmospheric pressure therapy in connection with healing a surgical wound includes a wound dressing dimensioned for positioning relative to a wound bed of a subject and a subatmospheric pressure mechanism dimensioned to be carried or worn by the subject. The subatmospheric pressure mechanism includes a housing having a control unit adapted to draw a vacuum, a container defining an internal chamber in fluid communication with the vacuum and the wound dressing to receive the wound exudates, a plunger received within the internal chamber and movable during actuation of the control unit and a hydrophobic filter associated with the plunger and permitting escape of gas from the container.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
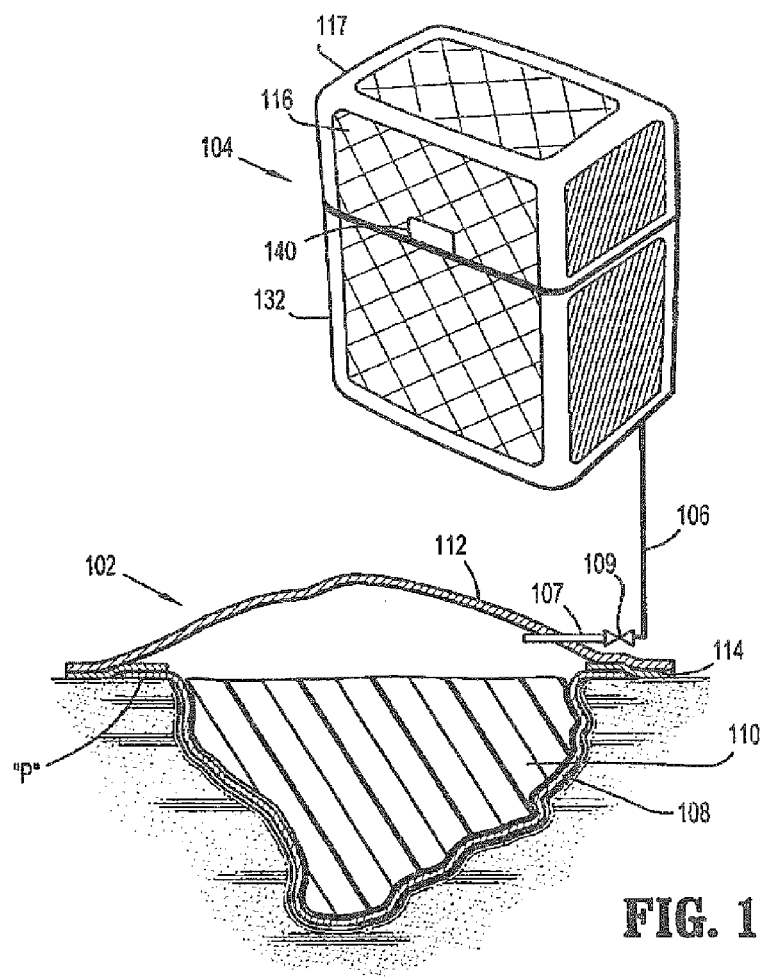
FIG. 1 is a side view in partial cross-section of the portable wound therapy system of the present disclosure illustrating the wound dressing and the subatmospheric pressure mechanism.

The wound therapy system of the present disclosure promotes healing of a wound via the use of a wound dressing and a portable subatmospheric pressure mechanism. Generally, the portable subatmospheric pressure mechanism applies subatmospheric pressure to the wound to effectively remove wound fluids or exudates captured by the composite wound dressing, and to increase blood flow to the wound bed and enhance cellular stimulation of epithelial and subcutaneous tissue. The wound therapy system is entirely portable, i.e., it may be worn or carried by the subject such that the subject may be completely ambulatory during the therapy period. The wound therapy system including the subatmospheric pressure mechanism and components thereof may be entirely disposable after a predetermined period of use or may be individually disposable whereby some of the components are reused for a subsequent therapy application.

The wound therapy system of the present disclosure promotes healing of a wound in conjunction with subatmospheric negative pressure therapy. The system may incorporate a variety of wound dressings, subatmospheric pressure sources and pumps, and collection canisters. The attached figures illustrate exemplary embodiments of the present disclosure and are referenced to describe the embodiments depicted therein. Hereinafter, the disclosure will be described by explaining the figures wherein like reference numerals represent like parts throughout the several views.

Referring initially to FIG. 1, wound therapy system 100 according to the present disclosure is illustrated. Wound therapy system 100 includes composite wound dressing 102 and subatmospheric pressure mechanism 104 in fluid communication with the wound dressing 102 through conduit, identified schematically as reference numeral 106.

Wound dressing 102 may includes several components, namely, wound contact layer or member 108, a wound packing member or filler 110 supported by the contact member 108 and outer layer or cover member 112. Wound contact member 108 is adapted to substantially conform to the topography of a wound bed "W". Wound contact member 108 is substantially porous or perforated to permit exudates to pass from the wound bed "W" through the wound contact member 108. The passage of wound exudates through the wound contact member 108 may be unidirectional such that wound exudates do not flow back to the wound bed "W". Unidirectional flow may be encouraged by directional apertures formed in contact member 108 or a lamination of materials having absorption properties differing from those of contact member 108. A non-adherent material may be selected such that contact member 108 does not tend to cling to wound bed "W" or surrounding material when it is removed. One exemplary material that may be used as a contact member 108 is sold under the trademark XEROFLOW® by Tyco Healthcare Group LP (d/b/a Covidien).

Wound packing member 110 of wound dressing 102 is intended to absorb and transfer wound fluid and exudates. Wound packing member 110 is conformable to assume the shape of any wound bed "W". Wound packing member 110 may be treated with agents such as polyhexamethylene biguanide (PHMB) to decrease the incidence of infection, or other medicants to promote healing of the wound. A suitable wound packing material 110 is the antimicrobial dressing sold under the trademark KERLEX® AMD by Tyco Healthcare Group LP (d/b/a Covidien).

Outer member or wound covering 112 encompasses the perimeter of the wound dressing 102 to surround wound bed "W" and to provide a liquid-tight seal around the perimeter "P" of the wound bed "W". For instance, the sealing mechanism may be any biocompatible adhesive bonded to the perimeter of wound covering 112. Thus, wound covering 112 may act as both a microbial barrier and a fluid barrier to prevent contaminants from entering wound bed "W" and for maintaining the integrity thereof.

Wound covering 112 is typically a flexible material, e.g., resilient or elastomeric, that seals the top of wound dressing 102 to prevent passage of liquids or contamination to and from the wound dressing 102. Wound covering 112 may be formed from a moisture vapor permeable membrane to promote the exchange of oxygen moisture between the wound bed "W" and the atmosphere. A membrane that provides a sufficient moisture vapor transmission rate is a transparent membrane sold under the trade name POLYSKIN® II by Tyco Healthcare Group LP (d/b/a Covidien). A transparent membrane permits an assessment of wound conditions to be made without requiring removal of the wound covering 112. Alternatively, wound covering 112 may comprise an impermeable membrane or a substantially rigid membrane.

Wound covering 112 may include a port or connector 107 in fluid communication with the interior of wound dressing 102 to facilitate connection of wound dressing 102 to conduit or tubing 106. Conduit 106 defines a fluid flow path leading through wound therapy system 100. Connector 107 may be configured as a rigid or flexible, low-profile component, and may be adapted to receive conduit 106 in a releasable and fluid tight manner. A hollow interior of connector 107 provides fluid communication between conduit 106 and the interior of wound dressing 102. Connector 107 may have a valve 109 built therein, e.g., a one-way, valve to permit exudates to flow in one direction only, i.e., away from wound dressing 102 toward subatmospheric pressure mechanism 104. Connector 107 may be provided as a pre-affixed component of wound dressing 102, as a component of conduit 106, or entirely separate and connected thereto by conventional means. Alternatively, connector 107 may be eliminated if other provisions are made for providing fluid communication between wound dressing 102 and conduit 106.

Conduit 106 extends from subatmospheric pressure mechanism 104 to provide fluid communication between the interior of the wound dressing 102 and vacuum source 118. Any suitable conduit may be used including those fabricated from flexible elastomeric or polymeric materials. Conduit 106 may connect to vacuum source 118 or other system components by conventional air tight means such as friction fit, bayonet coupling, or barbed connectors. The conduit connections may be made permanent, or alternatively a quick-disconnect or other releasable means may be used to provide some adjustment flexibility to the apparatus.

Figure 2:
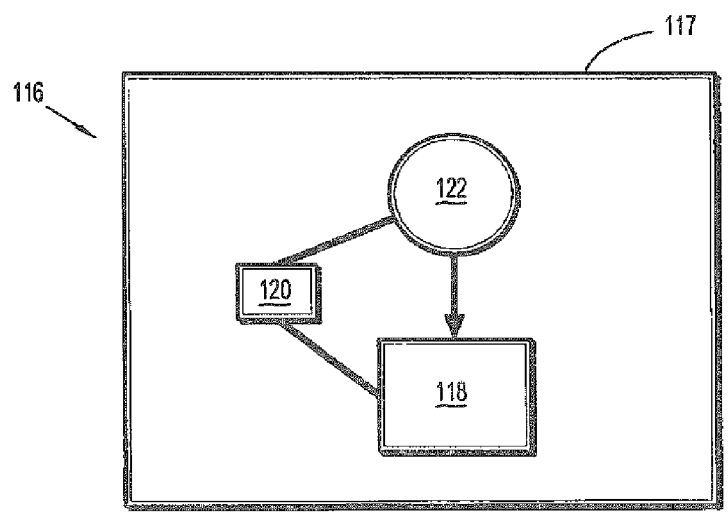
FIG. 2 is a schematic view illustrating the components of the control unit of the subatmospheric pressure mechanism.

Referring now to the schematic diagram of FIG. 2, in conjunction with FIG. 1, control unit 116 of subatmospheric pressure mechanism 104 will be discussed. Control unit 116 includes vacuum source or pump 118 disposed within housing 117, actuator or motor 120 disposed within housing 117 for activating the vacuum source 118 and power source 122 mounted relative to housing 117. Vacuum source or pump 118 generates or otherwise provides negative pressure to wound therapy system 100. Vacuum source or pump 118 may be a pump of the diaphragmatic, peristaltic or bellows type or the like, in which the moving part(s) draw exudates out of the wound bed "W" into the wound dressing 102 by creating areas or zones of decreased pressure e.g., vacuum zones with the wound dressing 100. This area of decreased pressure preferably communicates with the wound bed "W" to facilitate removal of the fluids therefrom and into the absorbent or non-absorbent packing member 110. One suitable peristaltic pump is the Kangaroo Enteral Pump manufactured by Tyco Healthcare Group LP (d/b/a Covidien).

Vacuum source or pump 118 may be a miniature pump or micropump that is biocompatible and adapted to maintain or draw adequate and therapeutic vacuum levels. The vacuum level of subatmospheric pressure achieved may be in the range of about 20 mmHg to about 500 mgHg. In some embodiments, about 75 mmHg and about 125 mmHg is desired or between about 35 mmHg and 75 mmHg may be desired. Vacuum source or pump 118 is actuated by actuator 120 which may be any means known by those skilled in the art, including, for example, AC motors, DC motors, voice coil actuators, solenoids, etc. Actuator 120 may be incorporated within pump 118.

On an exhaust side of vacuum source 118 fluid conduit 106 connects vacuum source 118 to collection canister 132. Conduit 106 may comprise the same material or construction along the entire length of the tubing or may assume an alternate form between vacuum source 118 and canister 132 than between wound dressing 102 and vacuum source 118. In the alternative, it may be separate tubing.

Power source 122 may be disposed within housing 117 or separately mountable to the housing 117. A suitable power source 122 includes alkaline batteries, wet cell batteries, dry cell batteries, nickel cadmium batteries, solar generated means, lithium batteries, NiMH batteries (nickel metal hydride) each of which may be of the disposable or rechargeable variety.

Referring again to FIG. 1, subatmospheric pressure mechanism 104 includes collection canister 132 which collects the exudates removed from the wound bed "W" during therapy through conduit, or tubing, 106. Collection canister 132 is releasably connected to housing 117 of control unit 116. Collection canister 132 may comprise any container suitable for containing wound fluids and is substantially rigid defining an internal chamber 133 in fluid communication with tubing 106. Collection canister 132 may contain an absorbent material to consolidate or contain the wound drainage or debris. In embodiments, at least a portion of collection canister 132 may be transparent to assist in evaluating the color, quality, or quantity of wound exudates. A transparent canister may thus assist in determining the remaining capacity of canister 132 or when the canister 132 should be replaced. In the alternative, collection canister 132 may be relatively flexible.

Figure 3:
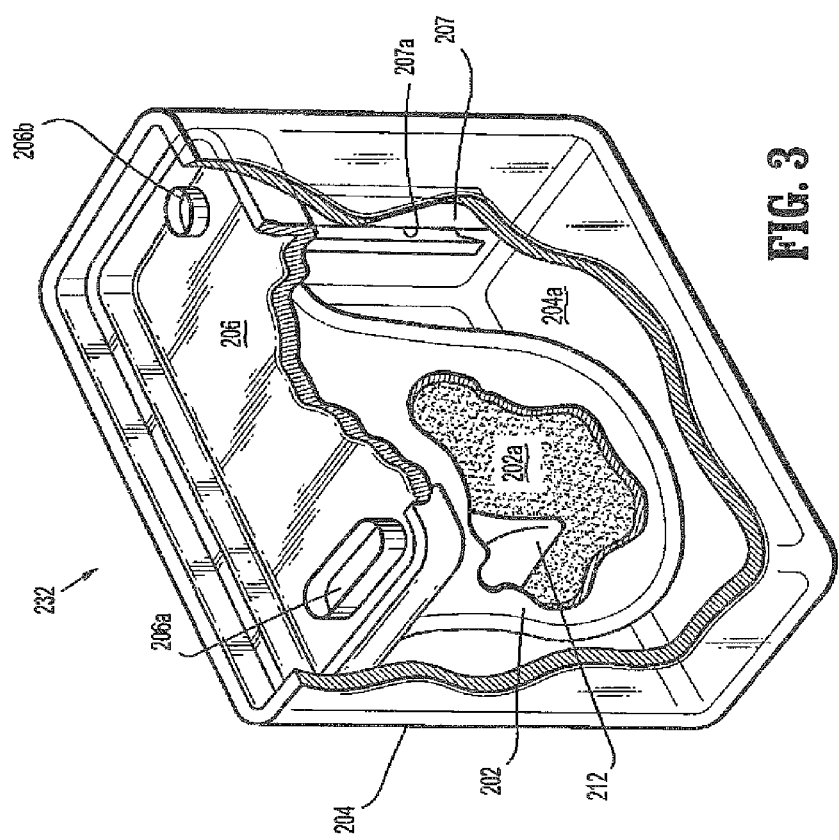
FIG. 3 is a partial cut-away perspective view of an embodiment of a collection canister according to the present disclosure.

Turning now to FIG. 3, an embodiment of a collection canister according to the present disclosure is shown generally as collection canister 232. Collection canister 232 includes a substantially rigid housing 204 defining a chamber 204a for receiving a collection bag 202. A cover 206 is configured to engage container 204 to for a sealed chamber 204a. Alternatively, cover 206 may be integrally formed with housing 117. Cover 206 defines an inlet port 206a and an outlet port 206b. Inlet port 206a is in fluid communication with wound dressing 102 and is configured to receive fluid "F" or exudates therefrom. A check valve 212 may be integrally formed with cover 206. Outlet port 206b is operably connected to vacuum source or pump 118. Outlet port 206 includes an extension 207. Extension 207 extends within chamber 204a of container 204. Extension 207 includes a channel 207a or other suitable configuration to ensure suction continues to be provided to chamber 204a as collection bag 202 expands to fill chamber 204a.

Collection bag 202 includes an expandable cavity 202a configured for receiving fluid "F". Collection bag 202 is constructed with a hydrophobic membrane or other suitable material capable of permitting gases to escape cavity 202a. Alternatively, collection bag 202 may have a hydrophobic vent (not shown). Collection bag 202 is maintained in fluid communication with inlet port 206a. It is envisioned that collection bag 202 may be integrally formed with cover 206.

In operation, suction from pump 118 is provided to chamber 204a of container 204 through outlet port 206b. As a vacuum builds within chamber 204a suction is provided to wound dressing 102 to draw fluid "F" from wound "W". As fluid "F" flows from wound "W" through inlet port 206a into cavity 202a of collection bag 202, any residual air or other gases in the system pass through collection bag 202. Cavity 202a expands to accommodate fluid "F" as the flow into collection bag 202 continues. Check valve 212 prevents fluid "F" from flowing from cavity 202a back towards wound dressing 102. Alternatively, check valve 212 may be formed on a distal end 106b of conduit 106. Collection bag 202 continues to expand as fluid "F" is drawn from wound "W". Channel 207a formed in extension 207 of outlet port 206b is configured to permit the continued flow of suction into chamber 204a, thereby allowing collection bag 202 to expand to fill chamber 204a. Once collection bag 202 and/or chamber 204a is filled, cover 206 may be removed and collection bag 202 may be emptied and/or replaced.

Figure 4:
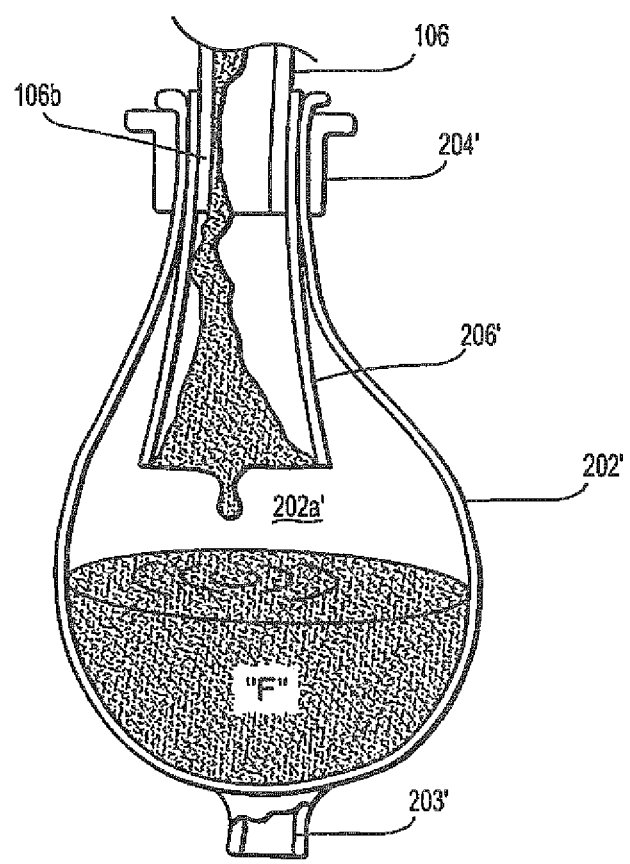
FIG. 4 is a cross-sectional side view of an embodiment of an expandable collection bag according to the present disclosure.

With reference now to FIG. 4, an alternate embodiment of a collection bag for use in collection canister 232 is shown as collection bag 202'. Collection bag 202' defines an expandable cavity 202a' for receiving fluids. A sealing band 204' maintains collection bag 202' in a sealed relationship with patient tube with inlet port 206a of cover 206. A check valve 212' is positioned on a distal end 106b of a conduit 106 to prevent back flow of fluid from collection bag 202' into conduit 106.

Collection bag 202' includes a bulb-shaped container constructed of rubber, polymer or other expandable material. As noted above, collection bag 202' defines an expandable cavity 202a'. Collection bag 202' further includes a hydrophobic plug 203' for releasing gas from within cavity 202a'. As fluid "F" flows from conduit 106 through check valve 212' and into cavity 202a' of collection bag 202', collection bag 202' expands to accommodate the additional fluid. Any gas trapped within cavity 202a' may be vented through hydrophobic plug 203'. Collection bag 202' may be removed from conduit 106 and discarded as necessary. It is envisioned that collection bag 202' may be reused. Collection bag 202' may optionally include a tie, draw string or other suitable closure device for sealing cavity 202a'.

Figure 5:
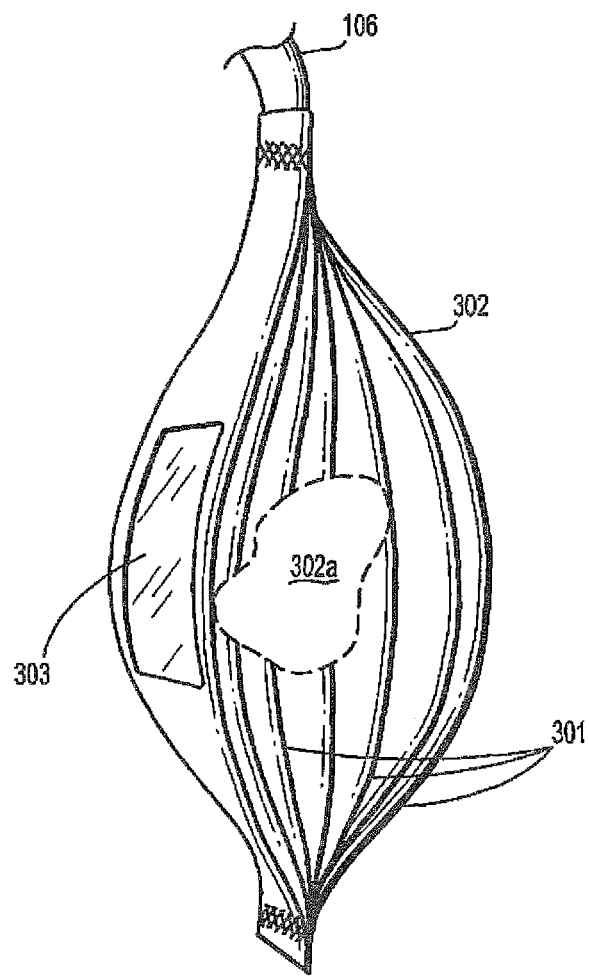
FIG. 5 is a perspective side view of another embodiment of an expandable collection bag according to the present disclosure.

Turning to FIG. 5, an alternate embodiment of a collection bag of the present disclosure is shown generally as collection bag 302. Collection bag 302 includes a pleated container constructed of a hydrophobic material, e.g. TYVEK. This construction permits any air or other gases trapped with the collection system to pass through collection bag 302 while collecting fluid "F" (FIG. 3) therein. Collection bag 302 defines an expandable cavity 302a for receiving fluids. In one embodiment, collection bag 302 is preferably configured to expand to fill chamber 204a of collection canister 232. Collection bag 302 may further include a window 303 for viewing the contents of cavity 302a. As fluid enters cavity 302a of collection bag 302, pleats 301 formed in collection bag 302 expand to increase the capacity of cavity 302a and accommodate the additional fluid.

Figure 6:
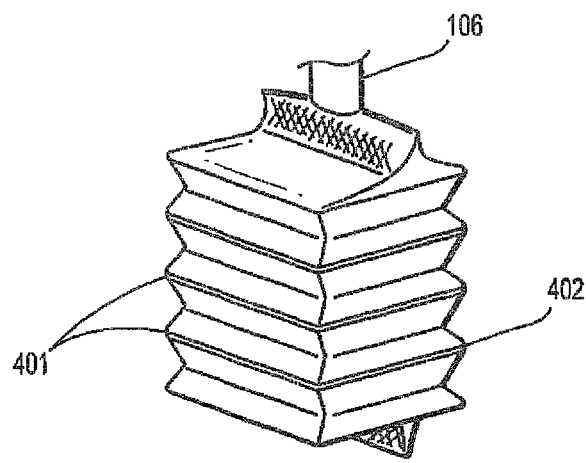
FIG. 6 is a perspective side view of yet another embodiment of an expandable collection bag according to the present disclosure.

With reference now to FIG. 6, another embodiment of a collection bag of the present disclosure is shown as collection bag 402. Collection bag 402 is constructed of hydrophobic material and includes accordion-like folds 401. Folds 401 are configured to expand as collection bag 402 fills with fluid "F" (FIG. 3).

Figure 7:
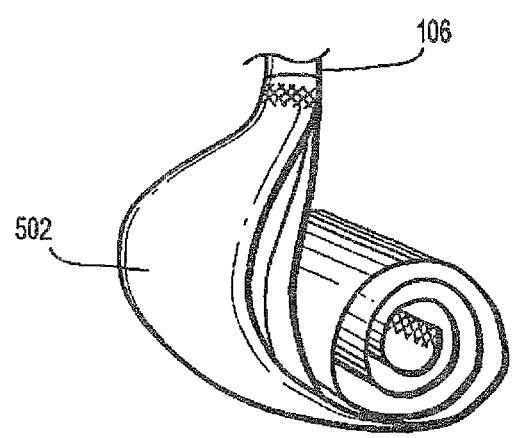
FIG. 7 is a perspective side view of still another embodiment of an expandable collection bag according to the present disclosure.

Turning now to FIG. 7, yet another embodiment of a collection bag is shown generally as collection bag 502. Collection bag 502 is constructed from hydrophobic material that is rolled. Collection bag 502 may include a window (not shown) for viewing the contents therein.

Figure 8:
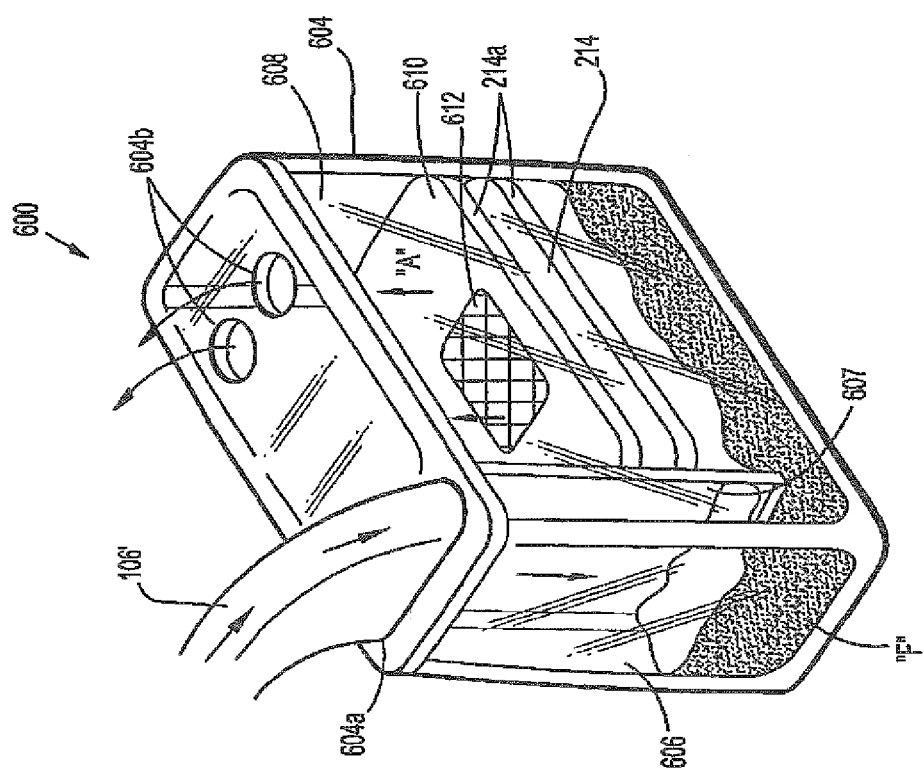
FIG. 8 is an interior perspective view of another embodiment of a collection canister according to the present disclosure.

Turning now to FIG. 8, another embodiment of the present disclosure is shown generally as collection device 600. Collection device 600 includes a container 604 defining a first chamber 606 in fluid communication with a second chamber 608 separated by a divider 607. Container 604 further includes an inlet port 604a in fluid communication with first chamber 606 and one or more outlet ports 604b in fluid communication with the second chamber 608. Inlet port 604a is operably connected to conduit 106'. Conduit 106' may include a check valve (not shown). Outlet ports 604b are operably connected to a source of suction not shown.

A plunger 610 is retained within second chamber 608 of container 604. Plunger 610 is a substantially planar member including a hydrophobic membrane 612 and a seal 214a extending about a perimeter 214 of plunger 610. Plunger 610 is configured to be advanced in the direction of arrow A as suction is applied to outlet ports 604b and air is removed from within second chamber 608. Alternatively, it is envisioned that plunger 610 may be attached to an advancement mechanism, including hydraulic, pneumatic and motorized cylinder, for advancing plunger 610. Movement of plunger 610 towards outlets 604b (direction of arrow "A") creates a vacuum in first chamber 606. The vacuum created in first chamber 606 provides suction to conduit 106'. As plunger 610 is drawn towards outlets 604b fluid "F" fills first and second chamber 606, 608. Residual air trapped within container 604 and/or conduit 106' is exhausted though hydrophobic membrane 612. Once first and second chambers 606, 608 are filled, conduit 106' is disconnected from container 604. Collection device 600 may include a valve or other mechanism (not shown) for draining container 604. Alternatively, collection device 600 may be discarded.

Figure 9:
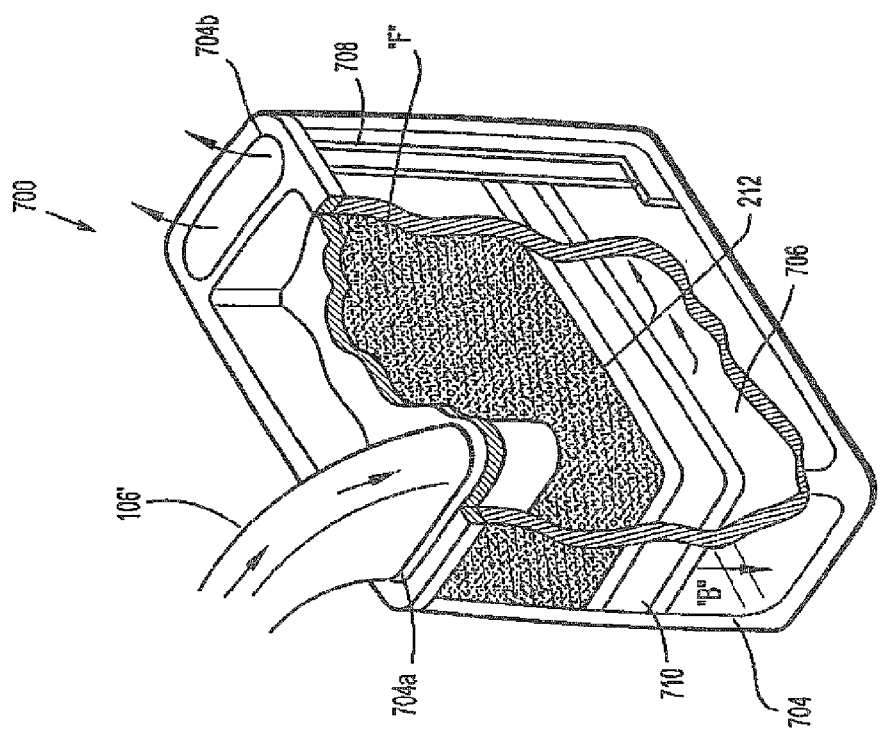
FIG. 9 is an interior perspective view of yet another embodiment of a collection canister according to the present disclosure.

Turning now to FIG. 9, another embodiment of the present disclosure is shown generally as collection device 700. Collection device 700 is substantially similar to collection device 600 and includes a container 704 having a first chamber 706 in fluid communication with a second chamber 708. First and second chambers 706, 708 are separated by a divider. An inlet port 704a fluidly communicates conduit 106' with first chamber 706. An outlet port 704b fluidly communicates second chamber 708 with a vacuum source (not shown). A plunger 710 is received within first chamber 706. Plunger 710 includes a hydrophobic membrane 212. Plunger 710 is configured to create a vacuum in first chamber 706 as plunger 710 is advanced in the direction of arrow "B". The vacuum in first chamber 706 causes fluid "F" to be drawn through conduit 106'. Once first chamber 706 is filled, conduit 106' is disconnected from container 704. Collection device 700 may include a valve or other mechanism (not shown) for draining container 704. Alternatively, collection device 700 may be discarded.

Figure 10A:
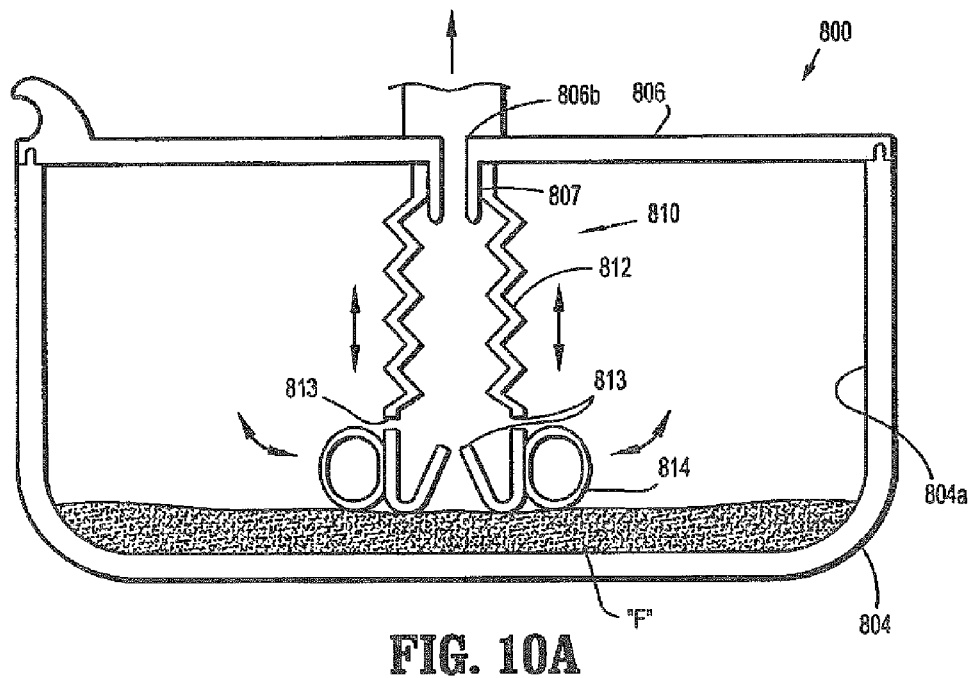
FIG. 10A is a cross-sectional side view of still another embodiment of an collection device according to the present disclosure.
Figure 10B:
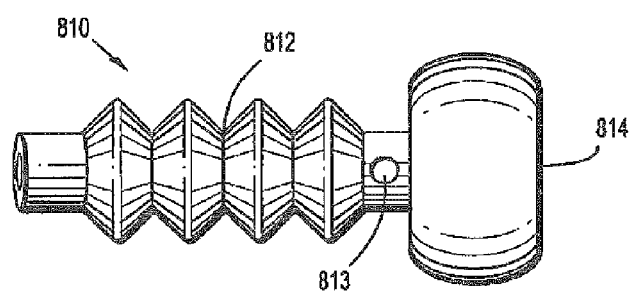
FIG. 10B is a side view of an intake mechanism of the collection device of FIG. 10A.

With reference now to FIGS. 10A and 10B, an alternate embodiment of the present disclosure is shown generally as collection canister 800. Collection device 800 includes a container 804 having a cover 806 and defining a substantially sealed chamber container 804a. An inlet port (not shown) may be formed in container 804 and/or cover 806. Cover 806 further includes an outlet port 806b configured for operable connection with a vacuum source. Cover 806 further includes a flange 807 extending inwardly from outlet port 806b. An intake mechanism 810 extends from flange 807 and is in fluid communication with outlet port 806b.

Intake mechanism 810 includes a bellows 812 and a float 814. Bellows 812 may be constructed of silicone or other suitable flexible material. Bellows 812 defines a passageway 812 therethrough in fluid communication with outlet port 806b. Bellows 812 includes openings 813 for receiving air from with chamber 804a. Float 814 may include an air bag, open cell material or other suitable material with a low mass. Float 814 may be affixed to an end of bellows 812. Alternatively, float 814 may be over-molded to bellows 812. Float 814 is configured to maintain at least one of openings 813 formed in bellows 812 above the level of fluid "F" as chamber 804a fills with fluid "F". Bellows 812 and float 814 are configured such that as container 804 is transported, i.e. tilted or inverted, collection device 800 continues to collect fluid "F".

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A system for treating a tissue site with reduced pressure, the system comprising:
   a wound dressing for placing proximate to a tissue site;
   a reduced-pressure source for providing reduced pressure; and
   a container configured to be fluidly coupled to the reduced-pressure source and a sealed treatment space formed under the wound dressing;
   wherein the container comprises:
      an interior space;
      a fluid inlet configured to be fluidly coupled to the sealed treatment space and the interior space;
      a reduced-pressure inlet configured to be fluidly coupled to the reduced-pressure source and the interior space; and
      a material adapted to allow gases to egress from the interior space separately from the reduced-pressure inlet while retaining liquids and maintaining reduced pressure; and
      wherein the container comprises a flexible pouch formed substantially from the material adapted to allow gases to egress from the interior space.

2. The system of claim 1, wherein the wound dressing comprises a wound filler for placing proximate to the tissue site.

3. The system of claim 1, wherein the wound dressing comprises a porous member for placing proximate to the tissue site.

4. The system of claim 3, further comprising a sealing member for forming a fluid seal over the porous member to form a sealed treatment space.

5. A container for receiving and processing body fluids, the container comprising:
- an interior space;
- a body fluid inlet fluidly coupled to the interior space;
- a reduced-pressure inlet fluidly coupled to the interior space; and
- a material adapted to allow gases to egress from the interior space separately from the reduced-pressure inlet while retaining liquids and maintaining reduced pressure; and wherein the container comprises a housing that comprises a flexible pouch formed substantially from the material adapted to allow gases to egress from the interior space.

6. A method for processing body fluids from a patient, the method comprising:
- causing the body fluids to enter into a container, wherein the container comprises:
  - an interior space;
  - a body fluid inlet fluidly coupled to the interior space;
  - a reduced-pressure inlet fluidly coupled to the interior space;
  - a material adapted to allow gases to egress from the interior space separately from the reduced-pressure inlet while retaining liquids and maintaining reduced pressure; and
  - wherein the container comprises a housing that comprises a flexible pouch formed substantially from the material adapted to allow gases to egress from the interior space; and
- permitting gases from the body fluids in the interior space to be evaporated and removed from the container using the material.

* * * * *